United States Patent
Sugimoto et al.

(10) Patent No.: US 10,414,724 B2
(45) Date of Patent: Sep. 17, 2019

(54) PHOTOCHEMICAL REACTION DEVICE, PHOTOCHEMICAL REACTION METHOD USING SAME, AND LACTAM PRODUCTION METHOD USING SAID METHOD

(71) Applicant: TORAY INDUSTRIES, INC., Tokyo (JP)

(72) Inventors: Takenori Sugimoto, Tokai (JP); Toru Takahashi, Otsu (JP); Kazuki Sugawara, Tokai (JP)

(73) Assignee: TORAY INDUSTRIES, INC., Tokyo (JP)

( * ) Notice: Subject to any disclaimer, the term of this patent is extended or adjusted under 35 U.S.C. 154(b) by 16 days.

(21) Appl. No.: 15/517,424

(22) PCT Filed: Sep. 17, 2015

(86) PCT No.: PCT/JP2015/076416
§ 371 (c)(1),
(2) Date: Apr. 6, 2017

(87) PCT Pub. No.: WO2016/056371
PCT Pub. Date: Apr. 14, 2016

(65) Prior Publication Data
US 2017/0298015 A1  Oct. 19, 2017

(30) Foreign Application Priority Data
Oct. 9, 2014  (JP) .................... 2014-208068

(51) Int. Cl.
| | |
|---|---|
| *C07D 201/04* | (2006.01) |
| *C07C 249/04* | (2006.01) |
| *B01J 19/12* | (2006.01) |
| *C07C 249/06* | (2006.01) |
| *C07B 61/00* | (2006.01) |

(52) U.S. Cl.
CPC ............ *C07D 201/04* (2013.01); *B01J 19/12* (2013.01); *B01J 19/127* (2013.01); *C07C 249/04* (2013.01); *C07C 249/06* (2013.01); *B01J 2219/0801* (2013.01); *B01J 2219/0877* (2013.01); *B01J 2219/1203* (2013.01); *C07B 61/00* (2013.01)

(58) Field of Classification Search
CPC .... C07D 201/04; C07C 249/04; B01J 19/127; B01J 19/12
See application file for complete search history.

(56) References Cited

U.S. PATENT DOCUMENTS

| | | | | |
|---|---|---|---|---|
| 5,055,693 | A * | 10/1991 | Grossman | B01D 59/34 250/373 |
| 8,324,595 | B2 | 12/2012 | Takahashi et al. | |
| 9,181,177 | B2 * | 11/2015 | Takahashi | C07C 249/06 |
| 9,932,296 | B2 * | 4/2018 | Takahashi | C07C 249/06 |
| 2011/0137027 | A1 * | 6/2011 | Aubert | C07D 227/087 540/464 |

FOREIGN PATENT DOCUMENTS

| | | |
|---|---|---|
| GB | 1010151 | 11/1965 |
| JP | 39022959 B1 | 10/1964 |
| JP | 44013498 B1 | 6/1969 |
| JP | 2002220350 A | 8/2002 |
| JP | 2005288288 A | 10/2005 |
| JP | 2008246355 A | 10/2008 |
| JP | 201006775 A | 1/2010 |
| JP | 2010006776 A * | 1/2010 |
| JP | 2010006776 A | 1/2010 |
| JP | 2010272472 A | 12/2010 |
| JP | 2011233366 A | 11/2011 |
| JP | 2011233431 A | 11/2011 |
| JP | 2012089755 A | 5/2012 |
| JP | 2012149055 A * | 8/2012 |
| JP | 2013200944 A | 10/2013 |
| WO | 2010058607 A1 | 5/2010 |

OTHER PUBLICATIONS

Knowles et al. Beilstein J. Org. Chem. 2012, 8, 2025-2052 (Year: 2012).*
International Search Report and Written Opinion for International Application No. PCT/JP2015/076416, dated Dec. 28, 2015, 6 pages.
Extended European Search Report for European Application No. 15849221.5, dated Feb. 14, 2018, 3 pages.

* cited by examiner

*Primary Examiner* — Matthew P Coughlin
(74) *Attorney, Agent, or Firm* — Ratnerprestia

(57) ABSTRACT

Provided is a photochemical reaction device wherein two partitions formed from an optically transparent material are arranged apart from each other between a light source and a reaction liquid, and an optically transparent fluid introduction/discharge means for introducing an optically transparent fluid between the partitions and discharging the fluid and a state change detection means for detecting a change in the state of the optically transparent fluid at the discharge side of the optically transparent fluid introduction/discharge means are provided. Also provided are a photochemical reaction method that uses the photochemical reaction device and a lactam production method that uses the photochemical reaction method. The present invention prevents decreases in the performance of the light source even when the optically transparent material in the photochemical reaction device is damaged, and makes it possible to reliably prevent ignition even if the reaction liquid is a flammable liquid.

9 Claims, 2 Drawing Sheets

FIG. 1

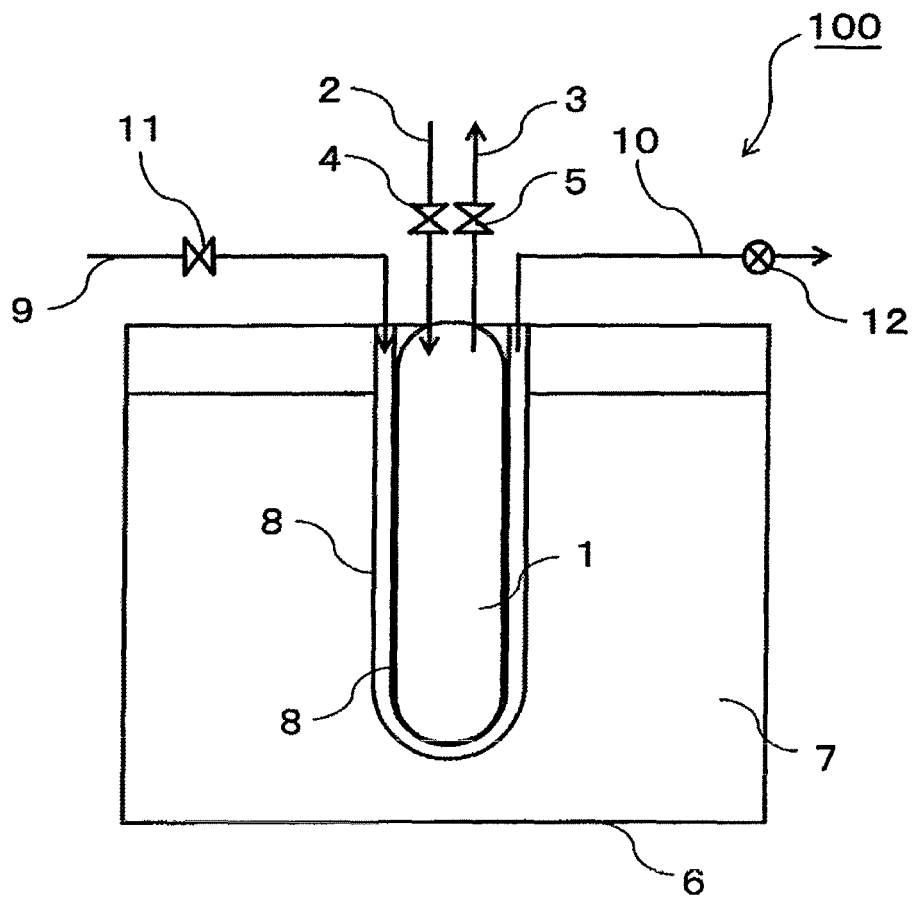

1 Light source
2 Light source coolant introduction line
3 Light source coolant discharge line
4 Light source coolant introduction line shutoff valve
5 Light source coolant discharge line shutoff valve
6 Photochemical reactor
7 Reaction liquid
8 Partition comprising optically transparent material
9 Optically transparent fluid introduction line
10 Optically transparent fluid discharge line
11 Optically transparent fluid shutoff valve
12 Optically transparent fluid abnormality detection device
100 Photochemical reaction device

FIG. 2

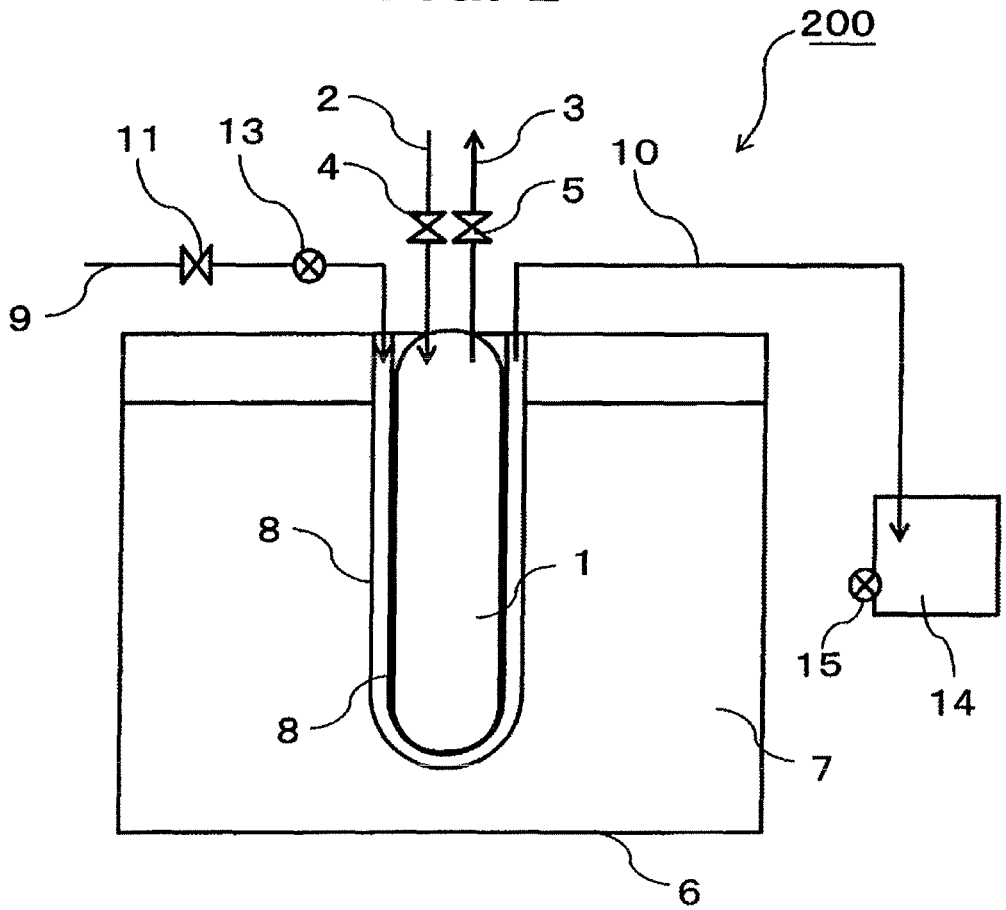

1 Light source
2 Light source coolant introduction line
3 Light source coolant discharge line
4 Light source coolant introduction line shutoff valve
5 Light source coolant discharge line shutoff valve
6 Photochemical reactor
7 Reaction liquid
8 Partition comprising optically transparent material
9 Optically transparent fluid introduction line
10 Optically transparent fluid discharge line
11 Optically transparent fluid shutoff valve
13 Optically transparent fluid flowmeter
14 Optically transparent fluid tank
15 Optically transparent fluid tank level gauge
200 Photochemical reaction device

PHOTOCHEMICAL REACTION DEVICE, PHOTOCHEMICAL REACTION METHOD USING SAME, AND LACTAM PRODUCTION METHOD USING SAID METHOD

CROSS REFERENCE TO RELATED APPLICATIONS

This is the U.S. National Phase application of PCT/JP2015/076416, filed Sep. 17, 2015, and claims priority to Japanese Patent Application No. 2014-208068, filed Oct. 9, 2014, the disclosures of each of these applications being incorporated herein by reference in their entireties for all purposes.

TECHNICAL FIELD OF THE INVENTION

The present invention relates to a photochemical reaction device which can more reliably and safely perform an isolation due to partitions made from an optically transparent material and provided between a light source and a reaction liquid, in particular, which is suitable in case where light emitting diodes are used as the light source, a photochemical reaction method using the same, and a method for producing a lactam using the method.

BACKGROUND OF THE INVENTION

A photochemical reaction indicates the whole of chemical reactions each in which molecules are brought into a state having a high energy level, a so-called excited state by photoirradiation, namely by making a radical reaction initiator absorb energy ascribed to the irradiated light, and the reaction is caused by the excited molecules. The photochemical reaction includes kinds of oxidation-reduction reaction by light, substitution-addition reaction by light, etc., and it is known that the applications include photo industry, copying technology, induction of photovoltaic power, and in addition, synthesis of organic compounds. Further, as unintentional photochemical reaction, photochemical smog and the like also belong to photochemical reaction.

For example, it is known that cyclohexanone oxime can be synthesized by photochemical reaction, and photonitrosation of cycloalkane is also a widely known technology at the present time.

As light sources for the photochemical reaction which have been used so far, in most cases, a lamp, in which mercury, thallium, sodium or another metal is enclosed in an environment of vacuum or close to vacuum, voltage is applied, and the emitted electron beam is irradiated to the enclosed metal, and the light emitting ascribed to electric discharge in gas or vapor condition is utilized, for example, a discharge lamp or a fluorescent lamp, is used as the light source.

For example, in case where a high pressure mercury lamp is used as a light source, the effective wavelength is 365 nm to 600 nm. However, in this type of discharge lamp using mercury, specific light emission energy due to mercury exists also in the wavelength region including ultraviolet rays of less than 365 nm. Therefore, for example, in case of having light emission energy in a short wavelength region including ultraviolet rays of less than 350 nm, because it is comparable to the dissociation energy of many chemical bonds, a reaction other than the purpose proceeds and promotes a side reaction, and a brown tar-like deposit is formed on the photoirradiation surface of the discharge lamp, thereby reducing the yield. Therefore, in order to cut the ultraviolet rays, a water-soluble fluorescent agent or a UV-cut glass is used.

In order to reduce such problems in a mercury lamp and improve the luminous efficiency, it is known that a thallium lamp exhibiting light emission energy effective to a wavelength of 535 nm and a sodium lamp exhibiting light emission energy effective to a wavelength of 589 nm are effective. By using a sodium lamp as a light source, the yield is dramatically increased and a stable reaction becomes possible. Further, by using a high-pressure sodium discharge lamp, the industrially effective wavelength is set at 400 to 700 nm, and the efficiency can be increased in the wavelength region of 600 nm to 700 nm. The peak wavelength in this range can be estimated to be about 580 to 610 nm. However, in order to improve the electric properties and starting of the discharge lamp, coexistence of mercury is inevitable, and a filter for cutting ultraviolet rays due to mercury is necessary. In particular, short wavelengths less than 400 nm generated by mercury are unnecessary wavelengths because they have excessive energy and cause unnecessary side reactions.

Furthermore, the sodium lamp has a peculiar light emission energy peak in a wavelength region including infrared rays having a wavelength of 780 to 840 nm, and its energy intensity is frequently comparable to the maximum light emission energy of the sodium lamp. Since the dissociation energy of nitrosyl chloride is about 156 J/mol, which is comparable to the light emission energy at a wavelength near 760 nm according to Einstein's law, the light energy is small in the longer wavelength region and the nitrosyl chloride does not dissociate, and therefore, it does not contribute to a reaction and causes a great energy loss.

On the other hand, light emitting diodes, also abbreviated as LEDs, have the advantage capable of converting electrical energy directly into light using semiconductors, and are attracting attention in terms of suppression of heat generation, energy saving, long life, and the like. Its history of development is still shallow, red LEDs were commercialized in 1962, LEDs such as blue, green and white were developed from around 2000, and they were commercialized for display and lighting uses. On the other hand, a discharge lamp used for a photochemical reaction has a very high output and a high luminous efficiency, but if it is attempted to obtain the light emission energy required for a photochemical reaction equivalent to that of a discharge lamp by LEDs, the required number of LEDs becomes enormous, and it has been considered that it is difficult to apply LEDs as a light source for a photochemical reaction, because problems in circuit design, LED heat countermeasure and cost remain. Furthermore, it is necessary to irradiate a reaction liquid with uniform light for the photochemical reaction, but the LED has a strong directivity and it is difficult to obtain the wavelength necessary for the reaction with a high efficiency, and also from this point of view, application of LEDs to the light source of the photochemical reaction has been considered to be difficult.

However, recently, as described in Patent document 1, there is an example in which photochemical reaction by LEDs is carried out using a small reaction apparatus, and moreover, as described in Patent documents 2 to 4, solution of the problems for enlarging a light-emitting body is being in sight.

PATENT DOCUMENTS

Patent document 1: JP-A-2010-006776
Patent document 2: JP-A-2011-233431

Patent document 3: JP-A-2012-089755
Patent document 4: JP-A-2013-200944

SUMMARY OF THE INVENTION

However, in the inventions so far, as a light source of a photochemical reaction, a light source module composed of a substrate mounting a light emitting diodes is used, and in order to physically separate the light source module and the reaction liquid, it is formed so as to make the reaction proceed via a partition comprising an optically transparent material. However, in case where a damage is caused on the partition comprising the optically transparent material, there is a possibility that performance degradation of the light source module due to contact with the reaction liquid may become a problem. Further, in case where the reaction liquid is a flammable liquid, there is a possibility that the light source module may become an ignition source.

Accordingly, an object of the present invention is to provide a photochemical reaction device which, in a photochemical reaction via a partition comprising an optically transparent material, can avoid performance degradation of a light source even when a damage is caused on the optically transparent material, and which can reliably prevent ignition even if the reaction liquid is a flammable liquid, a photochemical reaction method using the same, and a method for producing a lactam using the method.

As a result of earnest investigation to solve the above-described problems, it has been found that by providing partitions composed of two sheets of optically transparent materials between a light source module and a reaction liquid, it is possible to avoid contact between the light source and the reaction liquid, by flowing a fluid between these two partitions and detecting a change of the state of the fluid, it becomes possible to detect a damage of the optically transparent materials, and by stopping the light emission of the light source based on the detection, it becomes possible to reliably prevent ignition even if the reaction liquid is a flammable liquid, thereby completing the present invention.

In order to solve the above-described problems, aspects of the present invention include the following constitutions. Namely, (1) A photochemical reaction device characterized in that two partitions formed from an optically transparent material are arranged apart from each other between a light source and a reaction liquid, and an optically transparent fluid introduction/discharge means for introducing an optically transparent fluid between the partitions and discharging the fluid and a state change detection means for detecting a change in the state of the optically transparent fluid at the discharge side of the optically transparent fluid introduction/discharge means are provided.

(2) The photochemical reaction device according to (1), wherein the state change detection means comprises means for detecting a change in pressure or flow rate of the optically transparent fluid.

(3) The photochemical reaction device according to (1) or (2), wherein the optically transparent fluid is an optically transparent liquid, a tank is provided at the discharge side of the optically transparent fluid introduction/discharge means, and the state change detection means comprises a liquid level change detection means for detecting a change in the liquid level of the tank.

(4) The photochemical reaction device according to any one of (1) to (3), further comprises a light emission stop means for stopping at least the light emission of the light source when a value detected by the state change detection means deviates from a preset range.

(5) The photochemical reaction device according to any one of (1) to (4), wherein the light source comprises a light source module having a substrate mounted with a plurality of light emitting diodes.

(6) The photochemical reaction device according to (5), wherein a coolant introduction/discharge means for introducing and discharging a light source coolant into and from the light source module.

(7) A photochemical reaction method characterized by using the photochemical reaction device according to any one of (1) to (6).

(8) The photochemical reaction method according to (7), wherein at least the light emission of the light source is stopped when a value detected by the state change detection means deviates from a preset range.

(9) A photochemical reaction method characterized in that the photochemical reaction device according to (6) is used, and when the light emission of the light source module is stopped, the introduction/discharge of the coolant controlled by the coolant introduction/discharge means is stopped and the introduction of the optically transparent fluid controlled by the optically transparent fluid introduction/discharge means is stopped.

(10) The photochemical reaction method according to any one of (7) to (9), wherein a flammable liquid is used as the reaction liquid.

(11) The photochemical reaction method according to (10), wherein the flammable liquid is a cycloalkane.

(12) The photochemical reaction method according to (11), wherein a cycloalkanone oxime is produced by performing photoirradiation to the cycloalkane and a photo nitrosating agent.

(13) The photochemical reaction method according to (12), wherein the cycloalkanone oxime is cyclohexanone oxime or cyclododecanone oxime.

(14) The photochemical reaction method according to (12) or (13), wherein the photo nitrosating agent is nitrosyl chloride or trichloronitrosomethane.

(15) A method for producing a lactam characterized by using a cycloalkanone oxime produced by the photochemical reaction method according to any one of (12) to (14).

In the present invention, by irradiating the light from the light source to a reaction liquid via two sheets of partitions each formed from an optically transparent material, it becomes possible to reliably avoid contact between the light source and the reaction liquid, and further, by introducing and discharging an optically transparent fluid into and from between these two partitions and detecting a change of the state of the discharged fluid, it becomes possible to detect a damage of the optically transparent material from the change of the state, and by stopping the light emission of the light source based on the detection, it becomes possible to reliably prevent ignition even if the reaction liquid is a flammable liquid. In particular, even in case where the light source is composed of a light source module having a substrate on which light emitting diodes are mounted, since such effects can be reliably obtained, the present invention is extremely useful in case of making a light source from light emitting diodes.

BRIEF DESCRIPTION OF THE DRAWINGS

FIG. 1 is a schematic vertical sectional view of a photochemical reaction device according to an embodiment of the present invention.

FIG. 2 is a schematic vertical sectional view of a photochemical reaction device according to another embodiment of the present invention.

DETAILED DESCRIPTION OF EMBODIMENTS OF THE INVENTION

Hereinafter, embodiments of the present invention will be explained referring to figures.

FIG. 1 shows a photochemical reaction device 100 according to an embodiment of the present invention, and FIG. 2 shows a photochemical reaction device 200 according to another embodiment of the present invention in which a specified means is added to the device shown in FIG. 1. In the photochemical reaction device 100 shown in FIG. 1, a light source 1 (for example, a light source composed of a light source module having a substrate on which a plurality of light emitting diodes are mounted) is provided, and in the this embodiment, a light source coolant introduction line 2 and a light source coolant discharge line 3 are connected to the light source 1 as a light source coolant introduction/discharge means, thereby giving a water cooling function to the light source 1. To the respective lines 2, 3, a light source coolant introduction line shutoff valve 4 capable of stopping the introduction of the light source coolant and a light source coolant discharge line shutoff valve 5 capable of stopping the discharge of the light source coolant are provided. This light source 1 is inserted into a container or a tank-shaped photochemical reactor 6 in which a reaction liquid 7 is contained or flown, and served to the photochemical reaction by irradiating the light to the reaction liquid 7. In case where a light source module having a substrate on which a plurality of light emitting diodes are mounted is used as the light source 1, as the light emitting diode to be mounted, one capable of emitting a light having a wavelength required for the photochemical reaction among ultraviolet rays, visible lights and infrared rays may be selected. The shape of the light source module mounting the light emitting diodes is not particularly restricted, and the cross section may be any one of circular, polygonal, star shapes, etc.

Two partitions 8 formed from an optically transparent material are arranged apart from each other between the light source 1 and the reaction liquid 7, and the light source 1 and the reaction liquid 7 are isolated from each other via the two partitions 8. The optically transparent material forming the partition 8 is not particularly limited, and may be any of an organic material typically represented by a resin or an inorganic material typically represented by a glass may be employed. More concretely, acrylic resin, methacrylic resin, polycarbonate, polystyrene, polyvinyl chloride, polyester, borosilicate glass, soda-lime-silica glass, lead glass and the like can be used. Further, the shape of the partition 8 formed from an optically transparent material is not particularly restricted, and a test tube type as shown in FIG. 1, a cylinder type, a box type or the like may be selected appropriately depending upon the purpose. Two partitions 8 may have similar shapes or shapes different from each other. By giving a transmitted wavelength selectivity to the optically transparent material, for example, by using an acrylic resin therefor, it is also possible to prevent transmission of unnecessary wavelengths. Further, since the optically transparent material forming the outer partition 8 comes into contact with the reaction liquid 7, in case where the reaction liquid 7 has a corrosiveness, it is necessary to employ a corrosion resistant material such as a glass.

To a part between the two partitions 8, an optically transparent fluid introduction line 9 and an optically transparent fluid discharge line 10 are connected as an optically transparent fluid introduction/discharge means for introducing/discharging an optically transparent fluid. An optically transparent fluid shutoff valve 11 capable of stopping the introduction of the optically transparent fluid is provided to the optically transparent fluid introduction line 9, and an optically transparent fluid abnormality detection device 12 as a state change detection means for detecting a change in the state of the optically transparent fluid, in particular, detecting an abnormal state thereof, is provided to the optically transparent fluid discharge line 10. This optically transparent fluid abnormality detection device 12 detects a change in pressure or flow rate of the optically transparent fluid. Therefore, the optically transparent fluid abnormality detection device 12 can be constituted by a pressure detection means or a flow rate detection means. When the value detected by the optically transparent fluid abnormality detection device 12 deviates from a preset range, at least the light emission of the light source 1 is stopped, and a light emission stopping means (not shown) for that is provided in an electric circuit of the light source 1.

In the photochemical reaction device 200 shown in FIG. 2, the following means are added as compared with the device shown in FIG. 1. Namely, an optically transparent fluid flowmeter 13 capable of monitoring that the flow rate of the optically transparent fluid is within a predetermined flow rate range (or a flow rate control valve capable of controlling the flow rate within a predetermined range) is provided to the optically transparent fluid introduction line 9. Further, an optically transparent fluid tank 14 capable of temporarily storing the optically transparent fluid having been discharged is provided to the optically transparent fluid discharge line 10, and an optically transparent fluid tank level gauge 15 capable of detecting a liquid level, which varies depending upon the inflow amount into the optically transparent fluid tank 14, is provided to the tank 14. Since this optically transparent fluid tank level gauge 15, in particular, can detect a state in which the flow rate of the discharged optically transparent fluid light transmitting fluid deviates from a preset range and falls below the preset range, it can function as the state change detection means for detecting an abnormal state of the optically transparent fluid in the present invention.

In the photochemical reaction devices 100 and 200 shown in FIGS. 1 and 2, by irradiating the light from the light source 1 to the reaction liquid 7 via the two partitions 8 each composed of an optically transparent material, it is possible to reliably avoid contact of the light source 1 and the reaction liquid 7 and prevent the performance deterioration of the light source 1 more reliably. In addition, it becomes possible to introduce into and discharge from between these two partitions 8, detect a change in state of the discharged fluid, in particular, an abnormal change, and detect a damage of the optically transparent material forming the partitions 8 from the state change. By stopping at least the light emission of the light source 1 based on this detection, even if the reaction liquid 7 is a flammable liquid, it becomes possible to reliably prevent ignition. In particular, in case where the light source 1 comprises a light source module having a substrate mounted with light emitting diodes, such an effect can be securely obtained.

As the optically transparent fluid to be introduced into and discharged from between the partitions 8 formed from two optically transparent materials, it is preferred to use a nonflammable and optically transparent gas or liquid, for example, water or nitrogen. Further, in particular, in case where a liquid is used, by adding a substance, that absorbs light having a specific wavelength, to the liquid, it is also possible to remove the light having the specific wavelength, which is unnecessary for the reaction. Further, since the light irradiated from the light source 1 can be effectively utilized as the refractive indexes of the optically transparent material, the optically transparent fluid and the reaction liquid are closer to each other, it is desired that the optically transparent fluid is a liquid similarly to the reaction liquid.

Further, in the present invention, a damage to the optically transparent material may be detected from a change in the flow rate and pressure of the optically transparent fluid being discharged, but if the detection of the damage is performed only when an abnormal state is maintained for a certain period of time, it is possible to avoid erroneous detection due to a failure of the flowmeter or the pressure gauge.

By setting the pressure of the optically transparent fluid introduced into and discharged from between the partitions 8 formed from two optically transparent materials to be equal to or higher than the pressure of the reaction liquid 7 in the photochemical reactor 6, the outflow of the reaction liquid 7 to the discharge side, for example, the outflow of the reaction liquid 7 to the optically transparent fluid tank 14 in FIG. 2, can be prevented.

Further, by lowering the temperature of the optically transparent fluid introduced into and discharged from between the partitions 8 formed from two optically transparent materials, it becomes possible to remove heat from the light source 1, in particular, from the light source module using light emitting diodes, and an effect of suppressing deterioration of the light source module can be expected.

Further, by sealing an inert gas such as nitrogen inside the inner partition 8 formed from the optically transparent material at a condition of positive pressure, even in case where a damage is generated on the inner partition 8, it becomes possible to avoid contact of the light source 1 and the optically transparent fluid, thereby preventing performance degradation of the light source 1.

As the inert gas to be enclosed inside the inner partition 8 formed from the optically transparent material, rare gases such as helium, neon and argon can be exemplified, in particular, it is preferred to use nitrogen which can be easily and inexpensively available.

Thus, in case where inert gas is sealed inside the inner partition 8 formed from the optically transparent material, when the enclosed inert gas contains oxygen, since there is a possibility that oxidation deterioration of the light source 1, particularly the light source module using the light emitting diodes, may be caused, the oxygen concentration thereof is desired to be 2% or less, and desirably to be at an oxygen concentration of 1.5% or less as a more preferable condition.

In the photochemical reaction device 200 shown in FIG. 2, by installing the optically transparent fluid tank 14 at a place where there is no ignition source, in case where the reaction liquid 7 is flammable, particularly inflammable, even when it flows out into the optically transparent fluid tank 14, ignition can be avoided.

Further, as shown in FIGS. 1 and 2, if the optically transparent fluid shutoff valve 11 capable of stopping the introduction of the optically transparent fluid is provided to the optically transparent fluid introduction line 9, by blocking the introduction of the optically transparent fluid when a damage of the optically transparent material is detected, mixing of the optically transparent fluid into the photochemical reactor 6 can be avoided, and generation of impurities by side reaction can be prevented.

Furthermore, as shown in FIG. 2, if the optically transparent fluid flowmeter 13 is provided to the optically transparent fluid introduction line 9, when the flow rate at this part becomes a regulated value or more and the liquid level of the optically transparent fluid tank 14 becomes lower than a regulated value, by stopping the light emission of the light source 1, it is possible to detect a damage of the optically transparent material at a high accuracy and secure a safer state more reliably.

In the present invention, using the above-described photochemical reaction devices 100 and 200, various kinds of photochemical reaction methods can be carried out. For example, in a photochemical reaction method, the destination of the photoirradiation may be a liquid which contains carbon atoms. Namely, in the photochemical reaction method according to the present invention, at least one destination of the photoirradiation may be a raw material system composed of a liquid. The liquid served as a raw material is not particularly restricted as long as it is a liquid containing carbon atoms, and as a reaction liquid, a flammable liquid, for example, hydrocarbons such as alkane and cycloalkane can be exemplified.

In the present invention, although the cycloalkane is not particularly limited in the number of carbon atoms, for example, preferred are cyclopropane, cyclobutane, cyclopentane, cyclohexane, cycloheptane, cyclooctane, cyclononane, cyclodecane, cycloundecane, and cyclododecane. In particular, cyclohexane as a raw material of ε-caprolactam and cyclododecane as a raw material of ω-lauryllactam are preferred.

Using the above-described cycloalkane and photo nitrosating agent, cycloalkanone oxime is obtained by photochemical reaction due to the photo irradiation from the light source 1. As the photo nitrosating agent, for example, nitrosyl chloride or a mixed gas of nitrosyl chloride and hydrogen chloride is preferable. Besides, since any of the mixed gas of nitric monoxide and chlorine, the mixed gas of nitric monoxide, chlorine and hydrogen chloride, the mixed gas of nitrose gas and chlorine, etc. acts as nitrosyl chloride in the photochemical reaction system, it is not limited to these supply forms of the nitrosating agent. Further, trichloronitrosomethane obtained by photochemical reaction of nitrosyl chloride and chloroform may be used as a nitrosating agent. When the photochemical reaction is carried out in the presence of hydrogen chloride, the cycloalkanone oxime becomes its hydrochloride, but it may be in the form of hydrochloride as it is.

By the above-described photochemical reaction, it is possible to obtain cycloalkanone oxime which depends upon the carbon number of the cycloalkane. For example, cyclohexanone oxime is obtained by phot nitrosating reaction with nitrosyl chloride using cyclohexane. Further, cyclododecanone oxime is obtained by photo nitrosating reaction with nitrosyl chloride using cyclododecane.

<Method for Producing Lactam>

A lactam can be obtained by Beckmann rearrangement of the cycloalkanone oxime obtained by the photochemical reaction. For example, in the reaction of Beckmann rearrangement of cyclohexanone oxime, ε-caprolactam is obtained as shown by the following reaction formula [Chemical formula 1]. Further, ω-laurolactam is obtained in the reaction of Beckmann rearrangement of cyclododecanone oxime.

[Chemical formula 1]

C₆H₁₀NOH • 2 HCl + H₂SO₄ ⟶

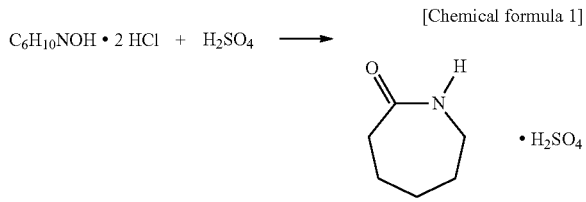

• H₂SO₄

In the above description, although the embodiments of the present invention have been explained with reference to FIGS. 1 and 2, these embodiments are shown as examples, and it is not intended to limit the scope of the present invention. It can be carried out in various forms, and can be simplified or changed without departing from the gist of the present invention. These embodiments and modifications thereof are also included in the scope of the present invention.

The present invention can be applied to any photochemical reaction using a light source, and in particular, it is useful for application to the production of cycloalkanone oxime and the production of lactam.

EXPLANATION OF SYMBOLS

1: light source
2: light source coolant introduction line
3: light source coolant discharge line
4: light source coolant introduction line shutoff valve
5: light source coolant discharge line shutoff valve
6: photochemical reactor
7: reaction liquid
8: partition formed from optically transparent material
9: optically transparent fluid introduction line
10: optically transparent fluid discharge line
11: optically transparent fluid shutoff valve
12: optically transparent fluid abnormality detection device
13: optically transparent fluid flowmeter
14: optically transparent fluid tank
15: optically transparent fluid tank level gauge
100, 200: photochemical reaction device

The invention claimed is:

1. A photochemical reaction method characterized by using a photochemical reaction device, wherein the photochemical reaction device comprises:
   a light source comprising a light source module having a substrate mounted with a plurality of light emitting diodes inserted into a photochemical reactor in which a reaction liquid is contained or flown and served to a photochemical reaction by irradiating the light from said light source to said reaction liquid,
   two partitions formed from an optically transparent material arranged apart from each other between said light source and said reaction liquid which is a flammable liquid,
   an optically transparent fluid introduction/discharge means for introducing an optically transparent fluid between said partitions and discharging said fluid and
   a state change detection,
   means for detecting a change in the state of said optically transparent fluid at the discharge side of said optically transparent fluid introduction/discharge means, and
   said state change detection means comprises means for detecting a change in pressure or flow rate of said optically transparent fluid, and
wherein the photochemical reaction method comprises the steps of:
   sealing an inert gas inside an inner partition of said two partitions at a condition of positive pressure; and
   irradiating the light from said light source to said reaction liquid to perform the photochemical reaction.

2. The photochemical reaction method according to claim 1, wherein at least the light emission of said light source is stopped when a value detected by said state change detection means deviates from a preset range.

3. The photochemical reaction method according to claim 2, wherein a coolant introduction/discharge means for introducing and discharging a light source coolant into and from said light source module is provided, and when the light emission of said light source module is stopped, the introduction/discharge of the coolant controlled by said coolant introduction/discharge means is stopped and the introduction of said optically transparent fluid controlled by said optically transparent fluid introduction/discharge means is stopped.

4. The photochemical reaction method according to claim 1, wherein said flammable liquid is a cycloalkane.

5. The photochemical reaction method according to claim 4, wherein a cycloalkanone oxime is produced by performing photoirradiation to said cycloalkane and a photo nitrosating agent.

6. The photochemical reaction method according to claim 5, wherein said cycloalkanone oxime is cyclohexanone oxime or cyclododecanone oxime.

7. The photochemical reaction method according to claim 5, wherein said photo nitrosating agent is nitrosyl chloride or trichloronitrosomethane.

8. The photochemical reaction method according to claim 1, wherein said inert gas is nitrogen.

9. A photochemical reaction method comprising using a photochemical reaction device having a light source, including a light source module having a substrate mounted with a plurality of light emitting diodes, inserted into the photochemical reaction device in which a reaction liquid is contained or flown,
   introducing an optically transparent fluid between partitions of the photochemical reaction device and discharging said optically transparent fluid from between said partitions of the photochemical reaction device;
   detecting a change in discharge pressure or discharge flow rate of said optically transparent fluid;
   sealing an inert gas at a condition of positive pressure inside an inner partition of two of the partitions of the photochemical reaction device arranged apart from each other between the light source and a flammable reaction liquid; and
   irradiating light from said light source to perform a photochemical reaction.

* * * * *